US00PP21577P2

(12) United States Plant Patent
Orard

(10) Patent No.: US PP21,577 P2
(45) Date of Patent: Dec. 21, 2010

(54) HYBRID TEA ROSE PLANT NAMED 'ORACLELON'

(50) Latin Name: *Rosa hybrida*
Varietal Denomination: ORAclelon

(75) Inventor: Pierre Orard, Feyzin (FR)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/589,859

(22) Filed: Oct. 29, 2009

(51) Int. Cl.
*A01H 5/00* (2006.01)

(52) U.S. Cl. ..... Plt./136
(58) Field of Classification Search ..... Plt./136, Plt./135
See application file for complete search history.

(56) References Cited

U.S. PATENT DOCUMENTS

PP8,496 P 12/1993 Meilland

*Primary Examiner*—Kent L Bell
(74) *Attorney, Agent, or Firm*—McKee, Voorhees & Sease, P.L.C.

(57) ABSTRACT

A new variety of Hybrid Tea rose suitable for garden decoration, having flowers of warm apricot coloration.

1 Drawing Sheet

Classification: The present invention relates to a new *Rosa hybrida* plant.

Variety denomination: The new plant has the varietal denomination 'ORAclelon'.

BACKGROUND OF THE INVENTION

This invention relates to a new and distinct variety of Hybrid Tea Rose. It has as its seed parent the variety known as 'MEIronsse' (U.S. Plant Pat. No. 8,496) and as its pollen parent the variety known as 'KORverpea' (not patented).

SUMMARY OF THE INVENTION

Among the features which distinguish the new variety from other presently available and commercial rose cultivars known to the inventor are the following combinations of characteristics: its entirely smooth peduncle, its many stamens, its very smooth rachis and petiole and its large warm apricot flower. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'ORAclelon' may be asexually propagated by cuttings, budding and grafting. The budding and grafting successfully occurred on the plant/rootstock *Rosa hybrida cv.* 'Dr. Huey' (not patented).

COMPARISON WITH PARENTS

The new rose may be distinguished from its seed parent, 'MEIronsse' by the following combination of characteristics: whereas 'ORAclelon' bears double flowers (about 25 to 35 petals) of warm apricot coloration, 'MEIronsse' bears double flowers of Indian orange coloration edged with capsicum red with significantly lower range of petals (about 25 to 27 petals).

The new variety may be distinguished from its pollen parent, 'KORverpea' by the following combination of characteristics: whereas 'ORAclelon' bears double flowers (about 25 to 35 petals) of warm apricot coloration. 'KORverpea' bears bicolor flowers of wine red with brass colored reverse with significantly heavier petalage (about 40 petals). The new variety has an upright medium height growing habit (about 100 to about 125 cm. in height), whereas the pollen parent has a significantly shorter growing habit (about 90 cm. in height).

COMPARISON WITH THE CLOSEST COMMERCIALLY AVAILABLE CULTIVAR

The new variety may be distinguished from its closest commercially available cultivar, 'FRYxotic' by the following combination of characteristics: whereas 'ORAclelon' bears double flowers (about 25 to 35 petals) of warm apricot coloration, 'FRYxotic' bears flowers of apricot pink coloration with significantly heavier petalage (about 36 to 40 petals). The new variety has an upright medium height growing habit (about 100 to about 125 cm. in height), whereas the closest commercially available cultivar has a bushy upright medium-tall height with a significantly taller growing habit (about 140 to about 170 cm in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly. Flowers are borne on strong short to medium length stems (about 20 to about 46 cm.). Outdoors, the plant blooms abundantly and nearly continuously during the growing season. The flowers have a slight fruity apple-like to pear-like fragrance.

BUD

The peduncle is about 1.7 to about 5.1 cm. in length, of average to somewhat heavy caliper (about 0.3 to about 0.5 cm. in diameter), and usually erect. It is entirely smooth with few hairs. Peduncle color is between 146B and 146C sometimes lightly suffused, especially on the side exposed to the sun, with between 183B and 187A.

Before the calyx breaks, the bud is about 1.4 to about 2.2 cm. in diameter at the widest point, about 1.8 to about 2.7 cm. in length, and pointed in shape. The surface of the bud bears few foliaceous appendages, usually with slender entire foliaceous parts extending beyond the tip of the bud about ¼ or more of its length. Bud color is between 146A and 146B sometimes lightly suffused, especially on the side exposed to the sun, with between 183B and 187B.

The sepals are about 2.8 to about 3.2 cm. in length and about 0.9 to about 1.1 cm. in width at the widest point. The outer surface color of the sepal is between 146A and 146B sometimes lightly suffused, especially on the side exposed to the sun, with between 183B and 187B. The inner surface color of the sepal is near 138B broadly bordered by near 137A. The inner surface of the sepal is covered with fine wooly tomentum; sepal margins are lined with some stipitate glands and hairs.

The receptacle of the flower is of moderately short to medium length (about 0.5 to about 0.7 cm.) and somewhat thin in caliper (about 0.8 to about 1.0 cm. in diameter). The receptacle is cup-shaped in form. Its surface is very smooth with very few hairs and with thick fleshy walls. The receptacle color is between 144A and 146B.

As the petals open (after the calyx breaks), the bud is about 2.0 to about 2.7 cm. in diameter at the widest point, about 2.9 to about 3.6 cm. in length, and moderately ovoid to somewhat pointed in form. The color of the under surfaces of the newly opened petals is between 33C and 31B. At the point where the petal attaches, there is a small zone of between 4A and 3B. On the upper surfaces of the newly opened petals, the color at the base of the petals is between 23B and 21B, gradually suffusing toward the center of the petals to between 25C and 26B. At the point where the petal attaches, there is a moderately small zone of between 12A and 13B.

BLOOM

When fully open, the bloom ranges from about 11.0 to about 14.9 cm. in diameter. Petalage is double with about 25 to 35 petals and about 2 to 4 petaloids irregularly arranged. When partially open, the bloom form is high centered to somewhat cupped, and the petals are moderately tightly spiraled to cupped with petal edges somewhat reflexed outward. When fully open, the bloom form is more cupped, and the petals are loosely cupped with petal edges very reflexed to moderately rolled outward.

PETALS

The substance of the petals is moderately heavy and of medium thickness, with upper surfaces satiny to somewhat shiny and under surfaces slightly shiny to matte. The petals are about 3.5 to about 5.8 cm. in length and about 2.7 to about 6.2 cm. in width at the widest point. Petal margins are entire.

The outer petals are nearly round to somewhat obovate in shape with rounded apices.

The inner petals are obovate in shape with rounded apices.

Petaloids are about 0.4 to about 3.1 cm. in length and about 0.3 to about 1.2 cm. in width at the widest point. Petaloids are irregularly shaped somewhat oblanceolate to subulate with rounded apices.

NEWLY OPENED FLOWER

The under surface color of the outer petals is between 25D and 26D. At the point where the petal attaches, there is a small zone of between 12B and 13C. On the upper surfaces of the outer petals, the color at the base of the petals is between 19A and 20A, gradually suffusing toward the center of the petals to between 29D and 19D. At the point where the petal attaches, there is a moderately small zone of between 12A and 13B.

The under surface color of the intermediate and inner petals is between 29B and 26B. On the upper surfaces of the intermediate and inner petals, the color at the base of the petals is between 22B and 23C, gradually suffusing toward the center of the petals to between 29C and 24D.

The under and upper surface colors of the petaloids are similar in coloration to the upper and under surfaces of the intermediate and inner petals.

The general tonality of the newly opened flower is between 22B and 23C at the base of the petals gradually suffusing toward the center of the petals to between 29C and 24D.

THREE-DAY-OLD FLOWER

The under surface color of the outer, intermediate and inner petals is between 27A and 27D. At the point where the petal attaches, there is a small zone of between 12B and 13C. On the upper surfaces of the outer, intermediate and inner petals, the color at the base of the petals is between 20B and 18A, gradually suffusing toward the center of the petals to between 29D and 155B. At the point where the petal attaches, there is a moderately small zone of between 12B and 13C.

The under and upper surface colors of the petaloids are similar in coloration to the upper and under surfaces of the intermediate and inner petals.

The general tonality of the three-day-old flower is between 20B and 18A at the base of the petals gradually suffusing toward the center of the petals to between 29D and 155B.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 160) and are arranged regularly about the pistils; a few are mixed with petaloids. The filaments are of long length (about 0.8 to about 1.4 cm.) most with anthers. Filaments are between 17C and 16A in color usually moderately suffused with near 53B. The anthers are somewhat small for the class and all open approximately at the same time. Anther color when immature is near 20A on the external part and near 12D on the internal part. Anther color at maturity is near 165C on the external part and near 200C on the internal part. Pollen is abundant and between 16D and 18B in color.

FEMALE REPRODUCTIVE ORGANS

Pistils vary in number (average about 95). The styles are moderately even, somewhat short in length (about 0.3 to about 0.6 cm.), average in caliper, and separated. Stigma color is between 16C and 18A. Style color is between 1C and 2C often heavily suffused with between 187B and 187C. Ovaries are all enclosed in the calyx.

Hips are of moderately long length (about 1.7 to about 2.3 cm.), pear-shaped in form, and between 25A and 28B in color when ripe. The hip surface is very smooth with thick fleshy walls. The sepals are fugacious, and usually straight in shape.

The seeds are irregularly rounded, smooth in texture, approximately 15 to about 27 per hip, about 0.4 to about 0.6 cm. in diameter at the widest point and between 163C and 162A in color.

FOLIAGE

The compound leaves are usually comprised of three to five leaflets and are borne abundantly. The five-leaflet leaves are about 7.5 to about 12.1 cm. in length and about 6.4 to about 9.9 cm. in width at the widest point, moderately leathery to somewhat crisp in texture, and semi-glossy in finish on the upper side and matte in finish in the under side. The terminal leaflets are about 3.5 to about 5.8 cm. in length and about 2.5 to about4.8 cm. in width at the widest point, shaped ovate with moderately acute to somewhat obtuse apices and rounded bases. Their margins are usually simply serrate.

The upper surface color of the mature leaf is between 137A and 147A. The under surface color of the mature leaf is between 147B and 148B. The upper surface color of the young leaf is between 146A and 152A, often moderately suffused, especially toward the leaf edge and the mid-rib, with between 187A and 183A. The under surface color of the young leaf is between 147B and 148B, often moderately suffused with between 187B and 183B.

The rachis is average to somewhat heavy in caliper and very smooth. The upper side is deeply grooved with few hairs and stipitate glands on the edges of the grooves. The under side of the rachis is very smooth sometimes with very few stipitate glands. The rachis color is near 146C on the under side and near 137B on the upper side.

The stipules are about 0.9 to about 1.4 cm. in length and moderately wide (about 0.5 to about 0.7 cm.) with somewhat long straight points that usually turn out at an angle of more than 45 degrees and often recurve toward the stem. The stipule color is near 137B.

The petiole is average to somewhat heavy in caliper and very smooth. The upper side is deeply grooved with few hairs and stipitate glands on the edges of the grooves. The under side of the petiole is very smooth sometimes with very few stipitate glands. The petiole is about 0.4 to about 1.2 cm. in length and about 0.1 to about 0.2 cm in diameter at the widest point. The petiole color is near 146C on the under side and near 137B on the upper side.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright medium height growing habit (about 100 to about 125 cm. in height and about 48 to about 58 cm. spread at the widest point), with full branching. It displays moderately vigorous growth and the canes are of medium size caliper for the class (about 1.1 to about 2.0 cm. in width at the widest point).

The color of the major stems is between 146A and 146B. They bear many large prickles that are about 0.7 to about 1.0 cm. in length. The large prickles are almost straight to angled slightly downward with a somewhat short narrow oval base; prickle color is between 164A and 165B. The major stem bears few small prickles of similar shape and coloration.

The color of the branches is between 146B and 147B. They bear some large prickles which are of similar size and shape to the large prickles on the major stems; prickle color is between 152D and 153A sometimes lightly suffused with between 187C and 187D. The branches bear few small prickles of similar shape and coloration.

The color of the new shoots is between 146B and 147B often heavily suffused with between 187B and 183B. They bear some large prickles which are of similar size and shape to the large prickles on the major stems; prickle color is between 152D and 153A often heavily suffused with between 187B and 187C. The shoots bear few small prickles of similar shape and coloration.

I claim:

1. A new and distinct Hybrid Tea rose plant of the variety substantially as described and illustrated herein.

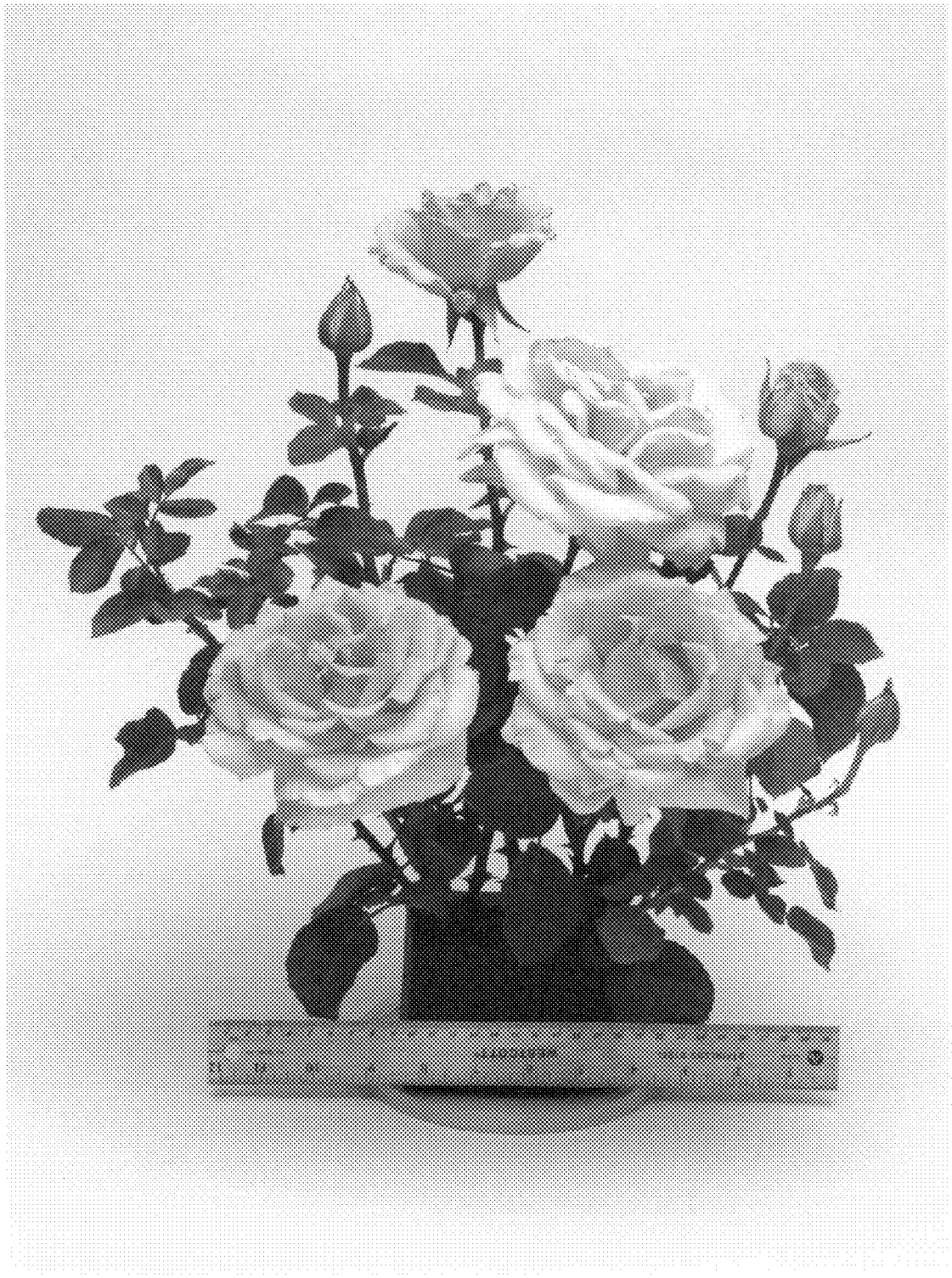

* * * * *